(12) United States Patent
Tass et al.

(10) Patent No.: US 8,473,059 B2
(45) Date of Patent: Jun. 25, 2013

(54) METHOD FOR TREATING DEMENTIA

(75) Inventors: Peter Alexander Tass, Titz (DE);
Hans-Joachim Freund, Ratingen (DE);
Volker Sturm, Meckesheim (DE)

(73) Assignees: Forschungszentrum Juelich GmbH,
Juelich (DE); Universitaet Zu Koeln,
Cologne (DE)

( * ) Notice: Subject to any disclaimer, the term of this patent is extended or adjusted under 35 U.S.C. 154(b) by 1180 days.

(21) Appl. No.: 12/346,916

(22) Filed: Dec. 31, 2008

(65) Prior Publication Data

US 2010/0168816 A1 Jul. 1, 2010

(51) Int. Cl.
*A61N 1/00* (2006.01)

(52) U.S. Cl.
USPC .................................................. 607/45

(58) Field of Classification Search
USPC .................................................. 607/45
See application file for complete search history.

(56) References Cited

U.S. PATENT DOCUMENTS 5,269,303 A * 12/1993 Wernicke et al. ............... 607/45
2006/0212089 A1 * 9/2006 Tass ................................ 607/45

* cited by examiner

*Primary Examiner* — Mark W Bockelman
(74) *Attorney, Agent, or Firm* — Andrew Wilford (57) ABSTRACT

A description is given of a method to treat dementia, in particular Alzheimer's disease, Lewy body dementia and vascular dementia, by means of electrical brain stimulation.

7 Claims, 5 Drawing Sheets

Fig. 13

METHOD FOR TREATING DEMENTIA

BACKGROUND OF THE INVENTION

This invention relates to the treatment of dementia and other neurodegenerative diseases, in particular Alzheimer's disease, Lewy body dementia and vascular dementia.

Dementia is the progressive decline in cognitive functions beyond what may be expected from normal aging. One form of dementia is Alzheimer's disease (AD), also called Alzheimer disease, senile dementia of the Alzheimer type (SDAT) or simply Alzheimer's. Alzheimer's disease is a progressive degenerative disease of the brain primarily diagnosed in people over 65 years of age. About 24 million people worldwide suffer from dementia and 60% of these people have Alzheimer's disease. It is expected that the number of Alzheimer patients is noticeably rising due to the increasing expectation of lifetime. Another type of dementia is Lewy body dementia, characterized by a different pathology with subcortical and cortical Lewy body formation. It has a high prevalence close to 30% and an incidence 4-6 times higher than in an age-matched general population. Compared with Alzheimer's disease, central cholinergic deficits occur earlier and are more pronounced and widespread in Lewy body dementia. But coexisting Alzheimer's disease pathology with amyloid plaques and neurofibrillary tangles is seen in 72% of these patients. Basal forebrain degeneration is also a key feature in the course of Alzheimer's disease and the impairment of basal forebrain input has been associated with the pathogenesis of protein aggregation. These results emphasize the key role of the basal nucleus of Meynert in both types of dementia. Another common form of dementia is vascular dementia, which is a group of syndromes characterized by different vascular pathologies and mechanisms.

Clinical presentation of Alzheimer's disease is characterized by loss of memory and decline of cognition, reasoning, judgment and orientation. As the disease progresses, motor, sensory and language abilities are also affected until there is global impairment of multiple cognitive functions. Alzheimer's disease is associated with neurofibrillary tangles and amyloid plaques.

For these and other reasons there is a need for the present invention.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION OF THE INVENTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

As employed in this Specification, the terms "coupled" and/or "electrically coupled" are not meant to mean that the elements must be directly coupled together; intervening elements may be provided between the "coupled" or "electrically coupled" elements.

Figure 1:
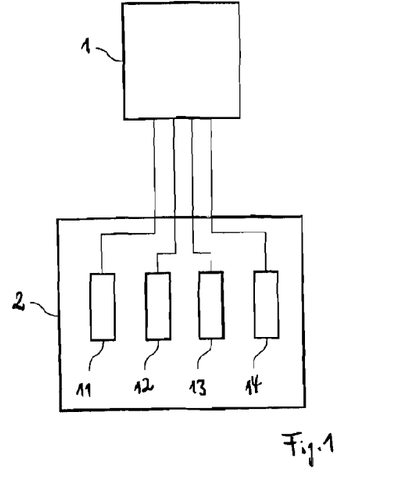
FIG. 1 schematically illustrates a device for brain stimulation including a stimulation signal generator and a stimulation unit according to one embodiment.

FIG. 1 schematically illustrates a device 100 for stimulating brain neurons. The device 100 includes a stimulation signal generator 1 and a stimulation unit 2 which is electrically coupled to the stimulation signal generator 1. The stimulation unit 2 contains at least one stimulation electrode. The stimulation unit 2 may also contain more than one stimulation electrode, for example N stimulation electrodes with N being a positive integer number (N=1, 2, 3, 4, 5, 6, 7, 8, 9, 10, . . . ). In the embodiment illustrated in FIG. 1, the stimulation unit 2 contains four stimulation electrodes 11, 12, 13 and 14 (N=4).

Before the stimulation is started, at least the stimulation unit 2 is implanted into a human body such that the stimulation electrodes 11 to 14 of the stimulation unit 2 are in contact with brain tissue. The stimulation signal generator 1 may also be implanted into the body and may be coupled to the stimulation unit 2 by appropriate cables. As an alternative the stimulation signal generator 1 may remain outside the body and communicates with the stimulation unit 2 via a radio link. The stimulation signal generator 1 generates electrical stimulation signals and feeds them into the stimulation unit 2 which administers the stimulation signals to the brain tissue via the stimulation electrodes 11 to 14.

Figure 2:
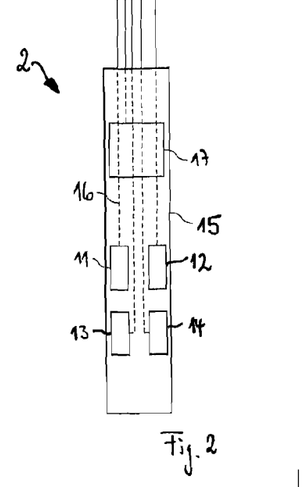
FIG. 2 schematically illustrates a stimulation unit according to one embodiment.

FIG. 2 schematically illustrates an embodiment of the stimulation unit 2. The stimulation unit 2 includes an biocompatible electrically insulating body 15 which holds the stimulation electrodes 11 to 14. The stimulation electrodes 11 to 14 are electrically conductive and may, for example, be made of a metal or a metal alloy. The stimulation electrodes 11 to 14 may be arranged in rows, columns, arrays or other configurations. They may have any suitable size and shape, for example they may be round, rectangular or square-shaped. During operation of the device 100 the exposed surfaces of the stimulation electrodes 11 to 14 are in electrical contact with nerve tissue. In the present embodiment each of the stimulation electrodes 11 to 14 can be accessed via a respective wire 16, i.e. each of the stimulation electrodes 11 to 14 may administer different stimulation signals.

The stimulation unit 2 may further include a reference electrode 17, the exposed surface of which may be larger than the surface of one of the stimulation electrodes 11 to 14. A reference potential is applied to the reference electrode 17 when stimulation signals are applied to the stimulation electrodes 11 to 14. Instead of the reference electrode 17, one or more of the stimulation electrodes 11 to 14 may be used for this purpose. In this case the stimulation signals are applied bipolar using a pair of stimulation electrodes for the application of each stimulation signal.

It may be provided that at least some of the stimulation electrodes 11 to 14 are used as sensors to record electrical signals of the brain issue. The function of these sensors is described in more detail further below.

The device 100 may be used to treat dementia and other neurodegenerative diseases, in particular Alzheimer's disease, Lewy body dementia and/or vascular dementia. The stimulation electrodes 11 to 14 are in contact with regions of the brain which are affected by one of these diseases, for example Alzheimer's disease, and which may include deposits of tangles and plaques, in particular neurofibrillary tangles and amyloid plaques. The regions of the brain which may be stimulated to treat dementia, in particular Alzheimer's disease, Lewy body dementia and vascular dementia, are, for example, the basal nucleus of Meynert, the perforant path and the fornix. The electrodes 11 to 14 may be either directly placed in one or more of the mentioned regions or in one or more regions which are connected to the one or more of the mentioned regions by nerve fibers.

The major neurotransmitter involved in the pathogenesis of Alzheimer's disease is acetylcholine. It facilitates activation of the cortex, increases intracortical neurotransmission and is involved in the septal-hippocampal pathway. It is crucial for mnemonic function as well as arousal, alertness and the broad tuning of cognitive functions in general. The major source for cortical cholinergic activation is the basal nucleus of Meynert, which is comprised by loosely, but in specific regions densely packed cholinergic cells. The nucleus is approximately disc-shaped and horizontally oriented. It extends between the anterior commissure and the optic tract and is subdivided into an anterior, an intermediate and a posterior section. The intermediate part has special relevance in Alzheimer's disease, since it innervates the orbito-frontal, the fronto-medial as well as the dorso-lateral prefrontal cortex. This part of the nucleus and its respective cortical target-areas undergo early degeneration in Alzheimer's disease. The basal nucleus of Meynert and in particular its intermediate part may be the target for the electrical stimulation as described in this specification.

The perforant path provides a connectional route in the brain from the entorhinal cortex to all fields of the hippocampal formation, including the dentate gyrus, all CA fields and the subiculum. It is crucial for mnemonic function and heavily affected in Alzheimer's disease. It arises mainly from entorhinal layers II and III. There is a major dichotomy with respect to the laminar origin and related terminal distribution: neurons in layer II project to the dentate gyrus and CA3, whereas layer III cells project to CA1 and the subiculum. Neuritic plaques and neurofibrillary tangles do not uniformly affect the hippocampal formation in Alzheimer's disease. The heaviest load of these pathogenic proteins is in the very parts of the hippocampal formation which receive the strongest innervation from the perforant path. Axons from the entorhinal cortex run within the perforant path and form the compact angular bundle. This structure provides the major activating input to the above described target areas within the hippocampus and the molecular layer of the dentate gyrus. It can be visualised with MRI and may be the target for electrical stimulation as described in this specification.

Figure 3:
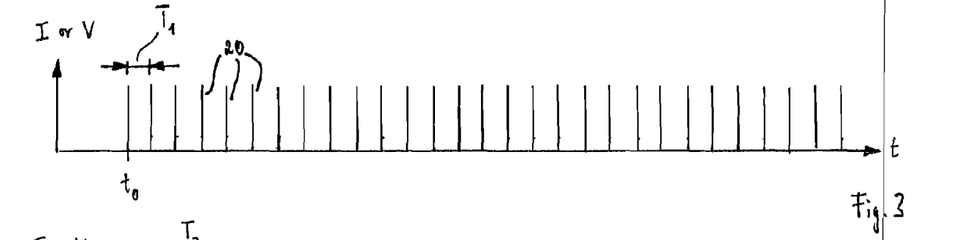
FIG. 3 schematically illustrates a method to treat dementia by administering stimulation signals having a frequency in the range between 80 and 200 Hz according to one embodiment.

The fornix of the brain is a C-shaped bundle of fibers, and carries signals from the hippocampus to the mammillary bodies and septal nuclei. The fibers originate in the hippocampus on each side of the brain (where they are also known as the fimbria); the separate left and right side are each called the crus of the fornix. The bundles of the fibers join in the midline of the brain, forming the body of the fornix. The inferior edge of the septum pellucidium (a membrane that separates the two lateral ventricles) is attached to the upper face of the fornix body. The body of the fornix travels anteriorly and divides again near the anterior commissure. The left and right parts reseparate, but there is also an anterior/posterior divergence. There is a reciprocal signal transmission between hippocampus and the cholinergic septal nuclei. The fornix may be the target for the electrical stimulation as described in this specification In FIG. 3 an embodiment of a method to treat dementia, in particular Alzheimer's disease, Lewy body dementia and/or vascular dementia, is schematically illustrated. The device 100 may, for example, be used to perform the method. As illustrated in FIG. 3 a series of current or voltage pulses 20 may be administered to the brain tissue via at least one of the electrodes 11 to 14. The pulses 20, which may be identical, may be periodically repeated with a frequency $f_1 = 1/T_1$ in the range between 80 and 200 Hz. Instead of 80 Hz being the lower limit of the range of the frequency $f_1$, the lower limit may also be 90, 100, 110, 120, 130, 140 or 150 Hz. Furthermore, instead of 200 Hz being the upper limit of the range of the frequency $f_1$, the upper limit may also be 190, 180, 170, 160, 150, 140, 130 or 120 Hz. The pulse train as shown in FIG. 3 may, for example, be continuously applied for more than 0.5, 1, 2, 5, 10, 20 or 30 hours. The application of the pulse train may, for example, be stopped not later than 0.5, 1, 2, 5, 10, 20 or 30 hours after the start of the stimulation.

Figures 4, 5:
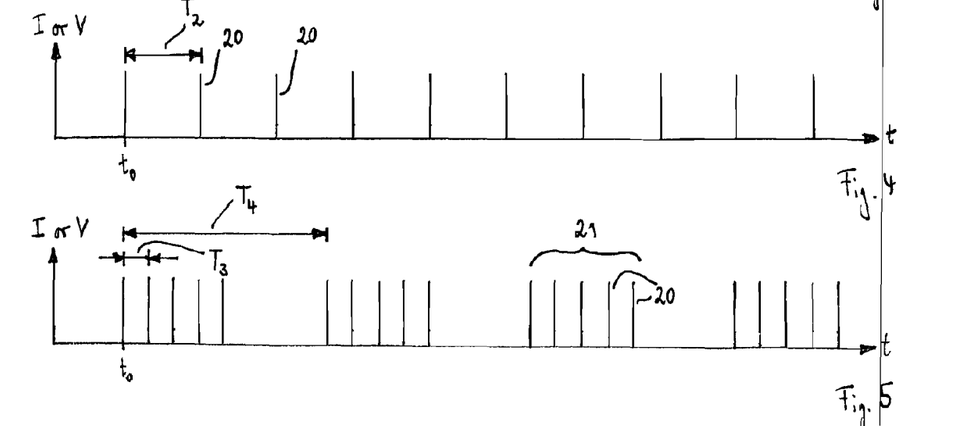
FIG. 4 schematically illustrates a method to treat dementia by administering stimulation signals having a frequency in the range between 2 and 50 Hz according to one embodiment.
FIG. 5 schematically illustrates a method to treat dementia by periodically administering bursts of pulses according to one embodiment.

In FIG. 4 a further embodiment of the method to treat dementia, in particular Alzheimer's disease, Lewy body dementia and/or vascular dementia, is schematically illustrated. The device 100 may, for example, be used to perform the method. As illustrated in FIG. 4 a series of current or voltage pulses 20 may be administered to the brain tissue via at least one of the electrodes 11 to 14. The pulses 20, which may be identical, may be periodically repeated with a frequency $f_2=1/T_2$ in the range between 2 and 80 Hz. Instead of 2 Hz being the lower limit of the range of the frequency $f_2$, the lower limit may also be 5, 10, 15, 20, 25, 30, 35, 40 or 45 Hz. Furthermore, instead of 80 Hz being the upper limit of the range of the frequency $f_2$, the upper limit may also be 75, 70, 65, 60, 55, 50, 45, 40, 35, 30, 25 or 20 Hz. The pulse train as shown in FIG. 4 may, for example, be continuously applied for more than 0.5, 1, 2, 5, 10, 20 or 30 hours. The application of the pulse train may, for example, be stopped not later than 0.5, 1, 2, 5, 10, 20 or 30 hours after the start of the stimulation.

In FIG. 5 a further embodiment of the method to treat dementia, in particular Alzheimer's disease, Lewy body dementia and/or vascular dementia, is schematically illustrated. The device 100 may, for example, be used to perform the method. According to the present embodiment burst 21 of current or voltage pulses 20 are repeatedly administered to the brain tissue via at least one of the stimulation electrodes 11 to 14. Each of the burst 21 may contain 1, 2, 3, 4, 5, 6, 7, 8, 9, 10, 11, 12, 13, 14, 15, 16, 17, 18, 19 or 20 or more pulses 20.

Within the same burst 21 the pulses 20 may be periodically repeated with a frequency $f_3=1/T_3$ in the range between 80 and 500 Hz. Instead of 80 Hz being the lower limit of the range of the frequency $f_3$, the lower limit may also be 90, 100, 110, 120, 130, 140, 150, 200, 250, 300 or 400 Hz. Furthermore, instead of 500 Hz being the upper limit of the range of the frequency $f_3$, the upper limit may also be 450, 400, 350, 300, 250 or 200 Hz. The pulses 20 within the same bursts 21 may be identical, but may also differ.

The bursts 20 may be periodically repeated with a frequency $f_4=1/T_4$ in the range between 1 and 50 Hz. Instead of 1 Hz being the lower limit of the range of the frequency $f_4$, the lower limit may also be 5, 10, 15, 20, 25 or 30 Hz. Furthermore, instead of 50 Hz being the upper limit of the range of the frequency $f_4$, the upper limit may also be 45, 40, 35, 30, 25 or 20 Hz. The sequence of the bursts 21 as shown in FIG. 5 may, for example, be continuously applied for more than 0.5, 1, 2, 5, 10, 20 or 30 hours. The application of the sequence of the bursts 21 may, for example, be stopped not later than 0.5, 1, 2, 5, 10, 20 or 30 hours after the start of the stimulation. The bursts 21 may be identical, but may also differ.

Some forms of dementia may be associated with a large population of brain neurons firing in a synchronized manner. In this case nerve cell groups or networks in certain regions of the brain, for example the basal nucleus of Meynert, the perforant path and the fornix, become pathologically active, for example excessively synchronous in their activity. In this case a large number of neurons generate action potentials synchronously and fire predominantly synchronously. Moreover, these neurons show a rhythmic activity, i.e. they have an oscillatory neuronal activity with an average frequency $f_{dementia}=1/T_{dementia}$ in the range between 1 and 30 Hz. With healthy individuals, by contrast, the neurons in these regions of the brain fire qualitatively differently, for example in an uncontrolled, non-synchronous manner.

In the course of the invention, it was discovered that in patients suffering from dementia, in particular Alzheimer's disease, Lewy body dementia and vascular dementia, excessively synchronous neurons showing a pathological neuronal rhythmic activity can be influenced by splitting the neuron population in at least two subpopulations having different phases in their neuronal activity.

Figure 6:
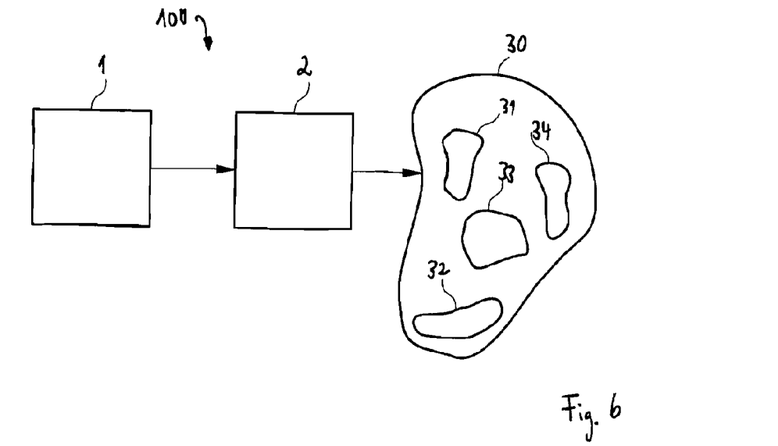
FIG. 6 schematically illustrates a method to treat dementia by resetting the neurons of subpopulations of a large population of neurons firing in a synchronized manner according to one embodiment.

FIG. 6 schematically illustrates the use of the device 100 for desynchronizing an excessively synchronous neuron population 30. The stimulation unit 2 is introduced into the brain region which causes the formation of the pathological pattern or into a region connected to the region to be desynchronized. Before the stimulation is started, a great number of the neurons to be stimulated fire essentially synchronously and thus have essentially a common phase in their neuronal activity. During the stimulation, each of the stimulation electrodes 11 to 14 outputs in its vicinity stimulation signals which effect a reset of the phase of the neuronal activity of the neurons stimulated by the respective stimulation electrode. The reset causes the phase of the neuronal activity of the stimulated neurons to be set to a predetermined phase value, for example 0°, or to a predetermined range of phase values, for example a range between 0° and 10° or other ranges. It is to be noted that after the phase reset not all of the stimulated neurons have exactly the same phase since there are always statistical fluctuations so that the phase values are statistically distributed to a certain degree. The predetermined phase value and the predetermined range of phase values do not dependent on the phase value the neurons have at the moment their phases are reset.

The neurons still fire synchronously shortly after the reset of their phases, however the neurons which have been stimulated with the same stimulation signal have a common phase which is different from the phases of the other neurons. Neurons having the same or similar phase form a so-called neuron subpopulation of the entire neuron population 30. Since the stimulation unit 2 includes four stimulation electrodes 11 to 14, four subpopulations 31, 32, 33 and 34 can be formed in the neuron population 30. For this purpose, each of the stimulation electrodes 11 to 14 outputs a stimulation signal capable of resetting the firing of the neurons stimulated therewith, and the stimulation signals output by each stimulation electrode 11 to 14 is time shifted (or phase shifted) to the stimulation signals output by the other stimulation electrodes. Thus each stimulation electrode 11 to 14 reset the phase of a respective one of the subpopulation 31 to 34 at a different point in time.

Shortly after the stimulation, the neuron population 30 is so influenced by the stimulation signals at the different stimulation sites that primary the total neuron population 30 is split into several subpopulations, which are the subpopulations 31 to 34 in the present embodiment. The neuronal activity within the same subpopulation is still synchronous, but the neurons of each subpopulation fire out of phase with the neurons of the other subpopulations. Because of the pathologically created interaction between neurons the state created by the stimulation is unstable, and the entire neuron population 30 quickly approaches a state of complete desynchronization. The desired state of complete desynchronization is thus not present immediately after the application of the stimulation signals, but typically develops over a short period of time.

The electrical stimulation may also result in a reorganization of the connections between the neurons in the stimulated neuronal network so that long lasting therapeutic effects may be achieved by using the stimulation methods described herein.

The stimulation signals administered by the stimulation electrodes 11 to 14 may be time shifted to each other in order to reset the phases of the subpopulations 31 to 34 at different point in times. Alternatively, the phases or the polarities of the stimulation signals may differ.

Figure 7:
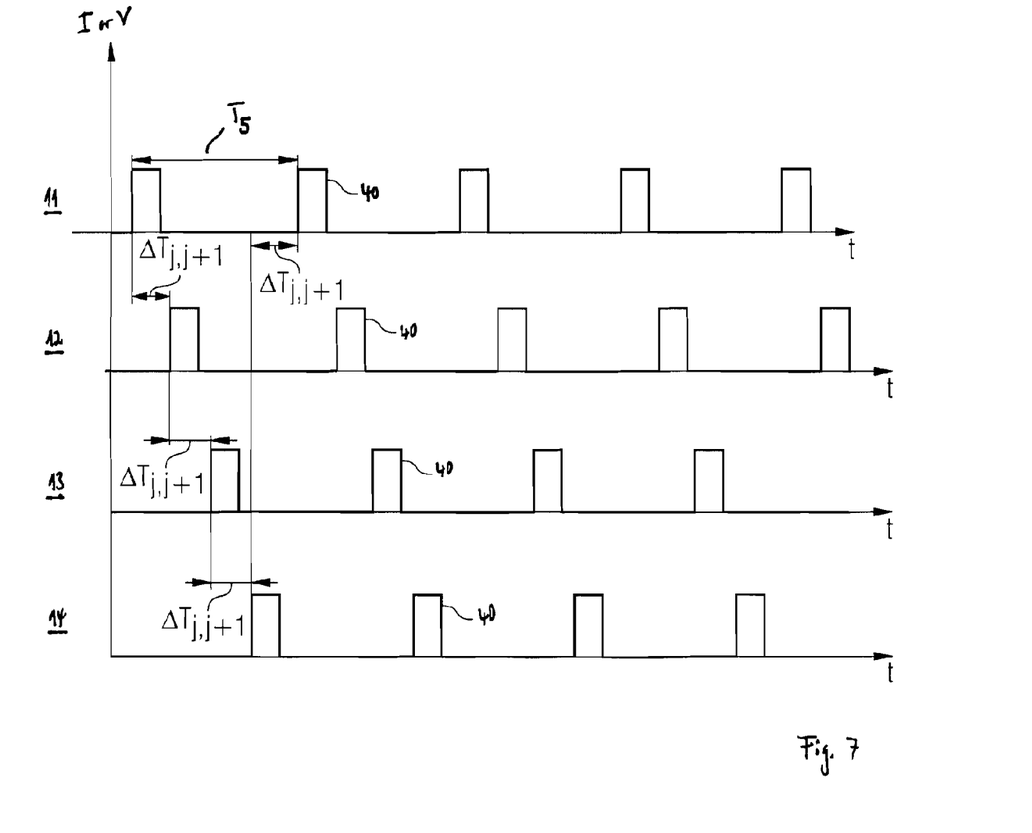
FIG. 7 schematically illustrates stimulation signals administered to the neurons of the subpopulations according to the embodiment illustrated in FIG. 6.

FIG. 7 schematically illustrates stimulation signals 40 administered to the neurons of the subpopulations 31 to 34 via the stimulation electrodes 11 to 14. In the embodiment shown in FIG. 7 each stimulation electrode 11 to 14 emits the stimulation signal 40 periodically to the respective neurons. The stimulation signals 40 are periodically repeated with a frequency $f_5=1/T_5$ in the range between 1 and 30 Hz an in particular in the range between 1 and 20 Hz or in the range between 5 to 20 Hz, but the frequency $f_5$ may also be outside these ranges. The frequency $f_5$ may be similar or identical to the frequency $f_{dementia}$ of the neurons to be desynchronized.

Successive stimulation signals 40 which are output by different stimulation electrodes may be delayed by a delay time $\Delta T_{j,j+1}$ as shown in FIG. 7. In the case the stimulation unit 2 includes N stimulation electrodes, the delay time $\Delta T_{j,j+1}$ between two successive stimulation signals 40 may be $\Delta T_{j,j+1}=T_5/N=1/(N*f_5)$. In the embodiment of FIG. 7 (N=4) the delay time $\Delta T_{j,j+1}$ is thus $1/(4*f_5)$. Other delay times $\Delta T_{j,j+1}$ may be also chosen.

Figure 8:
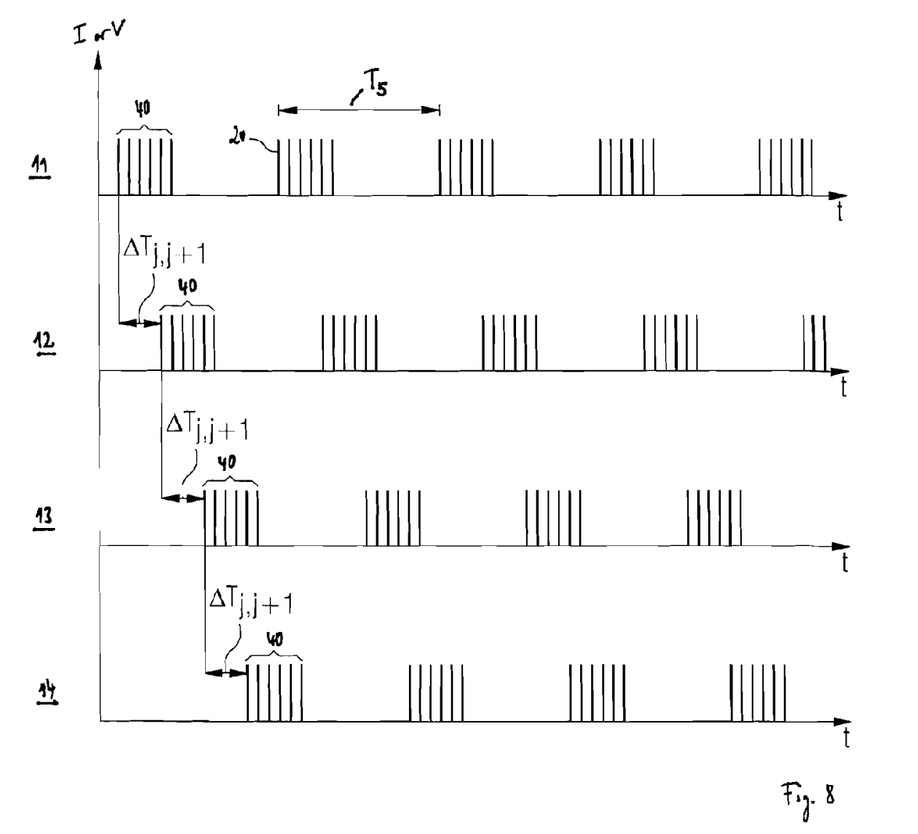
FIG. 8 schematically illustrates further stimulation signals administered to the neurons of the subpopulations according to the embodiment illustrated in FIG. 6.

The stimulation signals 40 may, for example, consists of current or voltage controlled pulses 20. Moreover, each stimulation signal 40 may be a burst 40 of identical pulses 20 as schematically illustrated in FIG. 8. Each burst 40 may contain 1 to 100 and in particular 2 to 10 pulses 20. The bursts 40 are administered via each electrode 11 to 14 as a sequence of at least 3, 5, 10, 20 or more bursts 40.

Figure 9:
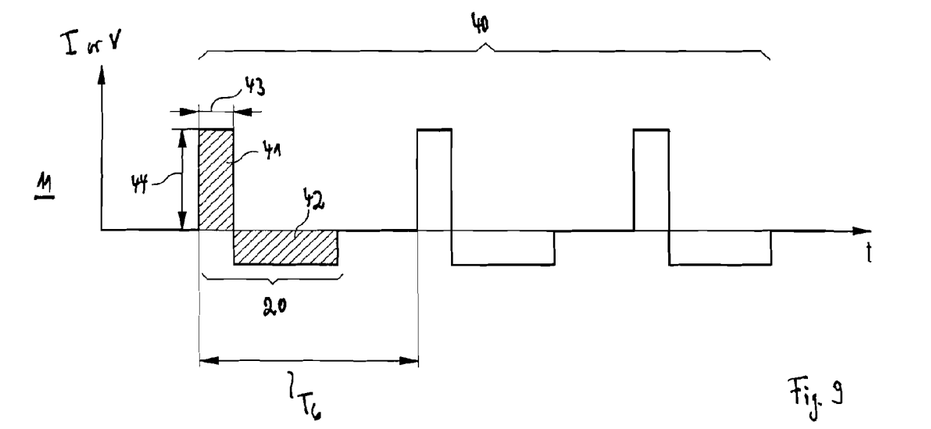
FIG. 9 schematically illustrates pulses used as stimulation signals according to one embodiment.

As an example, a burst 40 consisting of three charge balanced pulses 20 is schematically illustrated in FIG. 9. The individual pulses 20 are repeated with a frequency $f_6=1/T_6$ in the range between 50 and 500 Hz. Instead of 50 Hz being the lower limit of the range of the frequency $f_6$, the lower limit may also be 60, 70, 80, 90, 100, 110, 120, 130, 140, 150, 160, 170, 180, 190, 200, 250, 300 or 400 Hz. Furthermore, instead of 500 Hz being the upper limit of the range of the frequency $f_6$, the upper limit may also be 450, 400, 350, 300, 250, 200 or 150 Hz. In particular the frequency $f_6$ may be in the range between 80 and 150 Hz or in the range between 50 and 90 Hz. The pulses 20 may be current or voltage controlled and may be composed of a leading portion 41 and a trailing portion 42 flowing in the opposite direction than the leading portion 41. The length 43 of the leading portion 41 is in the range between 1 μs and 450 μs. The amplitude 44 of the leading portion 41 is in the case of current controlled pulses 20 in the range between 0 mA and 25 mA and in the case of voltage controlled pulses 20 in the range between 0 and 20 V. The amplitude of the trailing portion 42 is smaller than the amplitude 44 of the leading portion 41. The length of the trailing portion 42 is, however, longer than the length 43 of the leading portion 41. Ideally, the portions 41 and 42 have dimensions such that the same charge is transferred by both portions 41 and 42.

The details of the individual pulses 20 described above and illustrated in FIG. 9 may also be applied to the pulses 20 of the embodiments illustrated in FIGS. 3, 4 and 5.

Instead of using pulses, the stimulation signal generator 1 of the device 100 may also generate other types of stimulation signals, for example sinusoidal stimulation signals. Furthermore, it may be provided that the pulses do not have a rectangular shape as illustrated in FIG. 9, but have different shapes. For example, the trailing portions 42 of the pulses 20 shown in FIG. 9 may have exponentially declining amplitudes.

The strictly periodic pattern of the stimulation signals 40 as illustrated in FIG. 7 may also be varied. For example, the delay time $\Delta T_{j,j+1}$ between successive stimulation signals 40 may be varied and may be adjusted during stimulation.

Figure 10:
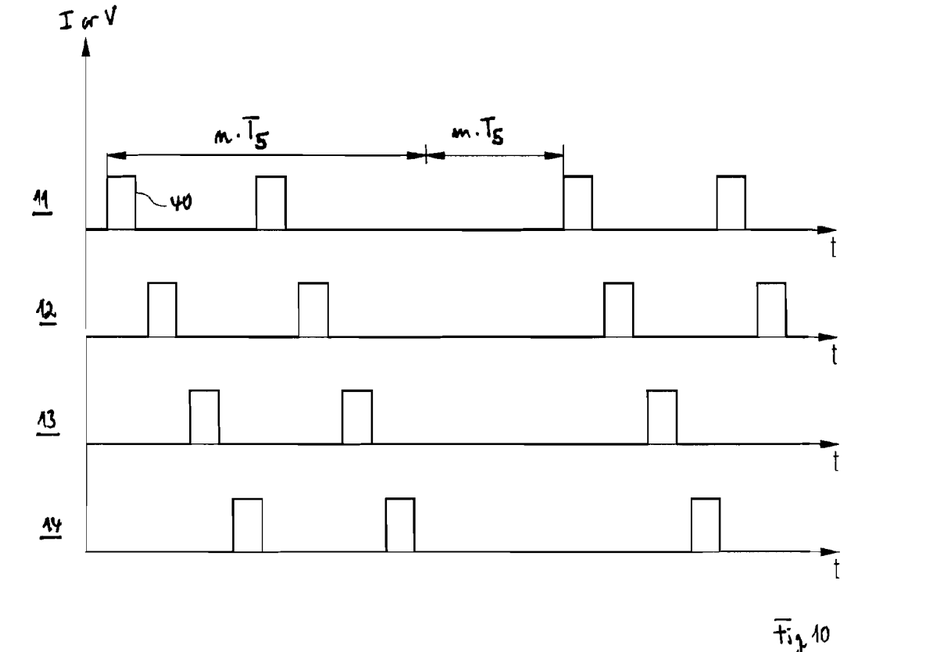
FIG. 10 schematically illustrates a variation of the stimulation signals illustrated in FIG. 7.

Moreover, the stimulation may be interrupted for a certain time. Such an interval during that stimulation is stopped is exemplarily illustrated in FIG. 10. The intermission may have any appropriate length and may be in particular a multiple of the period $T_5(=1/f_5)$. For example, the stimulation is carried out for n periods $T_5$ and is then interrupted for m periods $T_5$, wherein n and m are small integers, for example in the range between 1 and 10. This pattern may be periodically repeated or may be stochastically or deterministically modified.

Another variation of the stimulation method includes to vary the sequence of the stimulation signals 40. The sequence of the stimulation signals 40 may, for example, be varied stochastically or deterministically or both stochastically and deterministically.

Figure 11:
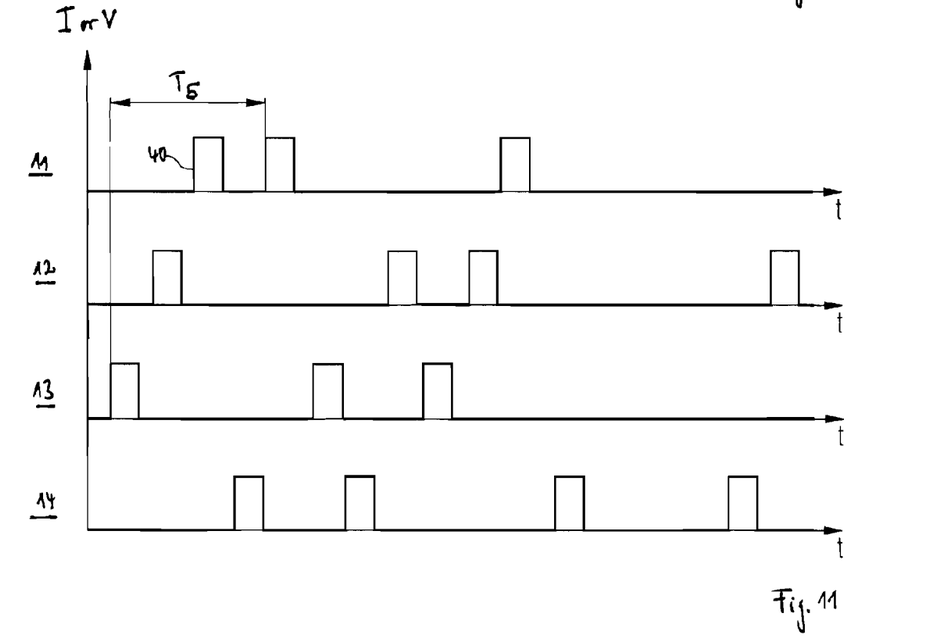
FIG. 11 schematically illustrates a further variation of the stimulation signals illustrated in FIG. 7.

As exemplarily illustrated in FIG. 11, the sequence of the stimulation electrodes 11 to 14 applying the stimulation signals 40 may, for example, be varied each period $T_5$. The sequence may, for example, be varied stochastically or deterministically or both stochastically and deterministically.

It may also be provided that only some of the stimulation electrodes 11 to 14 administer stimulation signals 40. The selection of stimulation electrodes may, for example, be varied every period $T_5$. This variation may, for example, be carried out stochastically or deterministically or both stochastically and deterministically.

Figure 12:
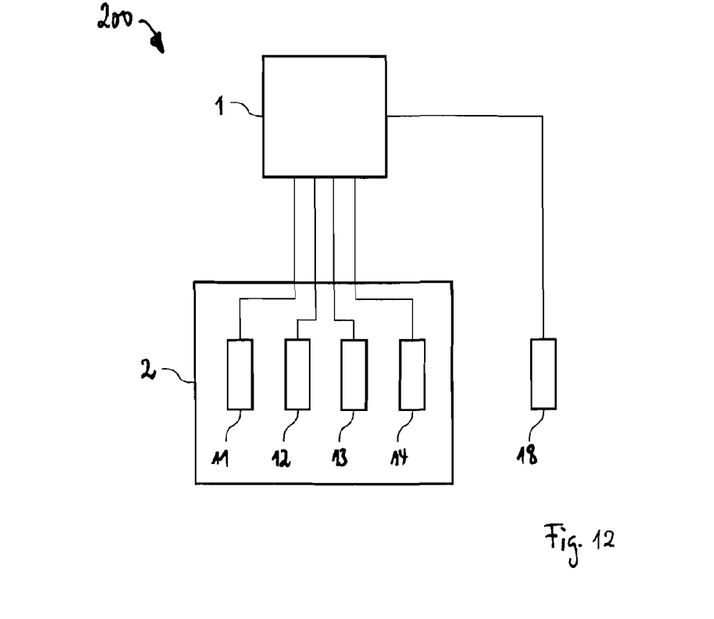
FIG. 12 schematically illustrates a device for brain stimulation including a stimulation signal generator, a stimulation unit and a sensor unit.

The stimulation of the brain tissue may be performed in an open-loop mode. In this mode the stimulation signal generator 1 generates the stimulation signals, feeds them into the stimulation unit 2 and the stimulation unit 2 administers the stimulation signals to the neurons. Furthermore, the stimulation device may be embodied to operate in a closed-loop mode. Such a device 200 is schematically illustrated in FIG. 12. The device 200 is identical to the device 100 in many ways, but includes an additional sensor unit 18 to record measurement signals from the patient. The sensor unit 18 may, for example, monitor the neuronal activity of the neuron population to be desynchronized.

The sensor unit 18 may include one or more non-invasive sensors, such as an EEG (electroencephalography) electrode, a MEG (magnetencephalography) sensor, an accelerometer, an EMG (electromyography) electrode and a sensor for monitoring blood pressure, respiration, skin resistance or heart frequency. The sensor unit 18 may also be implanted into the body of the patient. Such an invasive sensor unit 18 may, for example, include a deep brain electrode, a subdural or epidural brain electrode or a subcutaneous EEG electrode.

The stimulation signal generator 1 may receive the measurement signals monitored by the sensor unit 18 and may make a decision based on the measurement signals whether to start the stimulation or not. For that purpose, the stimulation signal generator 1 may detect the occurrence, the development and/or the strength of one or more pathological features in the measurement signals. For example, the amplitude of the neuronal activity or the amplitude of the band-passed neuronal activity may be measured and may be compared with a predetermined threshold value. If the amplitude of the (band-passed) neuronal activity exceeds the threshold value, the stimulation is started. Furthermore, parameters of the stimulation, such as the duration of the stimulation or the amplitude of the stimulation signals, may be set or adjusted according to the measurement signals.

According to one embodiment, the measurement signals recorded by the sensor unit 18 may be transferred to the stimulation unit 2 and may be directly used as the stimulation signals administered by one or more stimulation electrodes. Alternatively, the measurement signals may be linearly or non-linearly processed and the processed measurement signals may be used as the stimulation signals which are administered by one or more stimulation electrodes. The algorithm for processing the measurement signals is such that the pathological synchronous activity of the stimulated neurons decreases and the stimulation signals decrease with decreasing synchronous activity.

Linear processing of the measurement signals means for example that the measurement signals are filtered, amplified and/or delayed before they are fed into the stimulation unit 2.

In the following an example is given of a non-linear processing of the measurement signals. An equation of the stimulation signal S(t) is given by:

$$S(t) = K \cdot \overline{Z}^2(t) \cdot \overline{Z}^*(t-\tau), \quad (1)$$

wherein K is an amplification factor and $\overline{Z}(t)$ is a mean state variable of the measurement signal. $\overline{Z}(t)$ is a complex variable:

$$\overline{Z}(t) = X(t) + iY(t), \quad (2)$$

wherein X(t) is for example the neurological measurement signal. Since the frequencies are in the range of 10 Hz=$\frac{1}{100}$ ms=$1/T_\alpha$, the imaginary part Y(t) may be approximated by $X(t-\tau_\alpha)$ with $\tau_\alpha = T_\alpha/4$. Then equation (1) reads as follows:

$$S(t) = K \cdot [X(t) + iX(t-\tau_\alpha)]^2 \cdot [X(t-\tau) - iX(t-\tau-\tau_\alpha)] \quad (3)$$

Equation (3) may be rearranged:

$$S(t) = K \cdot [X(t)^2 \cdot X(t-\tau) + i2X(t) \cdot X(t-\tau_\alpha) \cdot X(t-\tau) - \quad (4)$$
$$X(t-\tau_\alpha) \cdot X(t-\tau) - iX(t-\tau-\tau_\alpha) \cdot X(t)^2 +$$
$$2X(t) \cdot X(t-\tau_\alpha) \cdot X(t-\tau-\tau_\alpha) + iX(t-\tau-\tau_\alpha) \cdot X(t-\tau_\alpha)]$$

The stimulation signal output by the stimulation unit 2 is the real part of equation (4):

$$\text{real}[S(t)] = K \cdot [X(t)^2 \cdot X(t-\tau) - X(t-\tau_\alpha) \cdot X(t-\tau) + 2X(t) \cdot X(t-\tau_\alpha) \cdot X(t-\tau-\tau_\alpha)] \quad (5)$$

Figure 13:
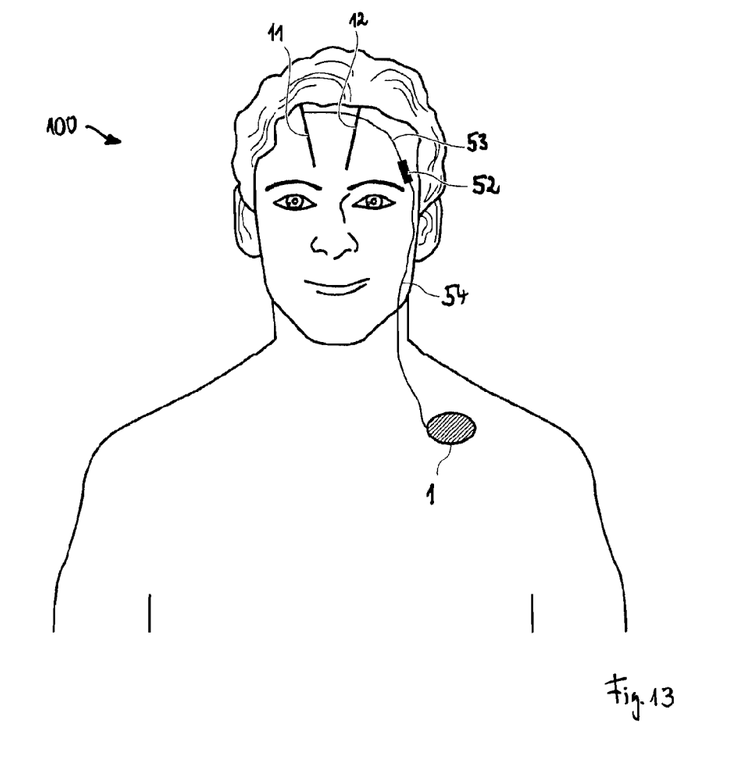
FIG. 13 schematically illustrates a device for brain stimulation implanted in a human body.

FIG. 13 schematically illustrates the device 100 during operation. For that, the device 100 has been implanted into the body of the patient. In the present embodiment two stimulation electrodes 11 and 12 have been introduced into the neuron population to be desynchronized or a region of the brain connected to the neuron population to be desynchronized. The stimulation electrodes 11 and 12 are coupled to a connector 52 by means of connection cable 53. A further connection cable 54 couples the connector 52 to the stimulation signal generator 1. In the present embodiment, all components of the device 100 are implanted in the body of the patient. The stimulation signal generator 1 may be situated on the chest muscle or in the borehole or in the upper abdomen. If the device 100 is embodied to be operated in closed-loop mode, it additionally contains a sensor unit.

In addition, while a particular feature or aspect of an embodiment of the invention may have been disclosed with respect to only one of several implementations, such feature or aspect may be combined with one or more other features or aspects of the other implementations as may be desired and advantageous for any given or particular application. Furthermore, to the extent that the terms "include", "have", "with", or other variants thereof are used in either the detailed description or the claims, such terms are intended to be inclusive in a manner similar to the term "comprise". Furthermore, it should be understood that embodiments of the invention may be implemented in discrete circuits, partially integrated circuits or fully integrated circuits or programming means. Also, the term "exemplary" is merely meant as an example, rather than the best or optimal. It is also to be appreciated that features and/or elements depicted herein are illustrated with particular dimensions relative to one another for purposes of simplicity and ease of understanding, and that actual dimensions may differ substantially from that illustrated herein.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of treating dementia, where a large population of brain neurons fire in a synchronized manner, the method comprising the steps of:
   implanting stimulation electrodes in a brain of a patient suffering from dementia with the stimulation electrodes either directly placed in one of the basal nucleus of Meynert and perforant path or in at least one region connected to at least one of the basal nucleus of Meynert and the perforant path by nerve fibers; and
   thereafter treating dementia by stimulating each of a plurality of subpopulations of the large population through the implanted electrodes with a respective stimulation signal each comprised of a burst of pulses having a respective predetermined frequency capable of resetting the firing of the neurons of the respective subpopulation with the burst fed to each subpopulation time shifted to the bursts fed to the other subpopulations such that the bursts reset the neurons of each subpopulation at a different point in time to fire out of phase with the neurons of the other subpopulations, the stimulation signals stimulating at least one of the basal nucleus of Meynert and the perforant path.

2. The method of claim 1, wherein each of the plurality of subpopulations is periodically stimulated with the burst of pulses.

3. The method of claim 2, wherein the bursts of pulses are repeated with a frequency f5 in the range between 1 and 30 Hz.

4. The method of claim 3, wherein an interval between two successive bursts of pulses administered to two different subpopulations is essentially 1/(f5*N) with N being the number of the stimulated subpopulations.

5. The method of claim 1, wherein the bursts of pulses are identical.

6. The method of claim 1, wherein the pulses within each of the bursts have a frequency in the range between 50 and 500 Hz.

7. The method of claim 1, wherein the method is used to treat at least one of Alzheimer's disease, Lewy body dementia and vascular dementia.

\* \* \* \* \*